US007906311B2

(12) United States Patent
David et al.

(10) Patent No.: US 7,906,311 B2
(45) Date of Patent: Mar. 15, 2011

(54) COTTON RAT LUNG CELLS FOR VIRUS CULTURE

(75) Inventors: Frederic R. David, Athens, GA (US); Sudhir K. Reddy, Fort Dodge, IA (US); Michael E. Tanner, Athens, GA (US)

(73) Assignee: Merial Limited, Duluth, GA (US)

( * ) Notice: Subject to any disclaimer, the term of this patent is extended or adjusted under 35 U.S.C. 154(b) by 0 days.

(21) Appl. No.: 10/391,498

(22) Filed: Mar. 18, 2003

(65) Prior Publication Data

US 2003/0219460 A1 Nov. 27, 2003

Related U.S. Application Data

(60) Provisional application No. 60/366,014, filed on Mar. 20, 2002.

(51) Int. Cl.
*C12N 7/00* (2006.01)
*C12N 7/02* (2006.01)
*C12N 5/07* (2010.01)
(52) U.S. Cl. ................ 435/235.1; 435/239; 435/353
(58) Field of Classification Search ............... 424/184.1, 424/204.1; 435/235.1, 237, 325, 352, 353, 435/456, 41, 70.1, 70.33
See application file for complete search history.

(56) References Cited

U.S. PATENT DOCUMENTS

| 5,151,267 | A | * | 9/1992 | Babiuk et al. | ............... | 424/186.1 |
|---|---|---|---|---|---|---|
| 5,476,778 | A | | 12/1995 | Chladek et al. | | |
| 6,136,594 | A | * | 10/2000 | Dalemans et al. | ......... | 435/320.1 |
| 6,290,968 | B1 | | 9/2001 | Clark et al. | | |
| 6,492,343 | B1 | * | 12/2002 | Reddy et al. | ..................... | 514/44 |
| 2002/0037274 | A1 | * | 3/2002 | Williams et al. | ............. | 424/93.2 |

FOREIGN PATENT DOCUMENTS

| CN | 1117742 | 2/1996 |
|---|---|---|
| EP | 94200964 | 4/1994 |
| EP | 0676467 | 10/1995 |
| EP | 0732340 | 9/1996 |
| EP | 1018557 | 7/2000 |
| GB | 1408437 | 10/1972 |
| JP | 06-228010 | 8/1994 |
| JP | 10-203998 | 8/1998 |
| WO | 97/49825 | 12/1997 |
| WO | 98/00165 | 1/1998 |
| WO | 99/53047 | 10/1999 |
| WO | 00/08165 | 2/2000 |
| WO | 00/61773 | 10/2000 |
| WO | 01/39797 | 6/2001 |
| WO | 01/60403 | 8/2001 |
| WO | WO 02/081653 | * 10/2002 |

OTHER PUBLICATIONS

Breker-Klassen et al., Journal of Virology, col. 69 No. 7, pp. 4308-4315 (Jul. 1995).*
Hooper et al., Journal of Veterinary Diagnostic Investigation, vol. 6 No. 1, pp. 13-15 (Jan. 1994)- abstract.*
Porter et al., Journal of Virology, vol. 65 No. 1, pp. 103-111 (Jan. 1991).*
Ali et al., Infection and Immunity, vol. 38 No. 2, pp. 610-619 (Nov. 1982).*
Mittal et al., Virology, vol. 213, pp. 131-139 (1995).*
Roberts et al., A novel epithelial cell from neonatal rat lung: isolation and differentiated phenotype, American Journal of Physiology, vol. 259 No. 6 (pt 1), pp. L415-425 (Dec. 1990).*
Duckmanton et al., Detection of Bovine Torovirus in Fecal Specimens of Calves with Diarrhea from Ontario Farms, Journal of Clinical Microbiology, vol. 36 No. 5, pp. 1266-1270 (May 1998).*
Zeng et al., Analysis of simian hemorrhagic fever virus (SHFV) subgenomic RNAs, junction sequences, and 5' leader, Virology, vol. 207 No. 2, pp. 543-548 (Mar. 1995).*
Birch et al., Human coronavirus OC43 causes influenza-like illness in residents and staff of aged-care facilities in Melbourne, Australia, Epidemiology and Infection, vol. 133 No. 2, pp. 273-277 (Apr. 2005).*
St.-Jean et al., Human respiratory coronavirus OC43: genetic stability and neuroinvasion. Journal of Virology, vol. 78 No. 16, pp. 8824-8834 (Aug. 2004).*
Papp et al., "Mucosal immunization with recombinant adenoviruses: induction of immunity and protection of cotton rats against respiratory bovine herpesvirus type 1 infection," Journal of General Virology, vol. 78, pp. 2933-2943 (Nov. 1997).*
STrube et al., "A gE deleted infectious bovine rhinotracheitis marker vaccine for use in improved bovine herpesvirus 1 control programs," Veterinary Microbiology, vol. 53 No. 1-2, pp. 181-189 (Nov. 1996).*
Heldens et al. "Clinical and virological evaluation of the efficacy of an inactivated EHV1 and EHV4 whole virus vaccine (Duvaxyn EHV1,4). Vaccination/challenge experiments in foals and pregnant mares," Vaccine vol. 19 No. 30, pp. 4307-4317 (Jul. 2001).*
Sato et al., "Varicella-Zoster Virus Open Reading Frame 2 Encodes a Membrane Phosphoprotein That Is Dispensable for Viral Replication and for Establishment of Latency," Journal of Virology, vol. 76 No. 7, pp. 3575-3578 (Apr. 2002).*
Rosenfeld et al., "Adenovirus-Mediated Transfer of a Recombinant α1-Antitrypsin Gene to the Lung Epithelium in Vivo ," Sceince, vol. 252 No. 5004, pp. 431-434 (Apr. 1991).*
Baca-Estrada et al. Induction of mucosal immunity in cotton rats to haemagglutinin-esterase glycoprotein of bovine coronavirus by recombinant adenovirus. Immunobgy 1995, 86: 134-140.
Hoffmann et al. The pulmonary epithelial cell line L 2 as a new model for an inducible nitric oxide synthase expressing distal airway epithelial cell. Biochem Biophys Res Comm 1995, 217: 575-583.
Braun et al. Compatibility of plasmids expressing different antigens in a single DNA vaccine formulation. Journal of General Virology 1998, 79: 2965-2970.
Langley et al. HIV type-1 infection of the cotton rat (*Sigmodon fulviventer* and *S. hispidus*. Proceedings of the National Academy of Science USA1998, 95: 14355-14360.

* cited by examiner

*Primary Examiner* — Zachariah Lucas

(74) *Attorney, Agent, or Firm* — Judy Jarecki-Black; Thomas J. Kowalski, Esq.; Merial Limited

(57) ABSTRACT

A cotton rat cell line, uses of cotton rat cells for growing, propagating, or culturing organisms, pathogens or viruses, such as PRRSV, and uses of the resultant organisms, pathogens or viruses, are disclosed.

18 Claims, No Drawings

COTTON RAT LUNG CELLS FOR VIRUS CULTURE

RELATED APPLICATIONS/INCORPORATION BY REFERENCE

This application claims priority from U.S. provisional application Ser. No. 60/366,014, filed on Mar. 20, 2002, incorporated herein by reference. The foregoing application, and all documents cited therein or during its prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

This invention relates to a new cell line and uses thereof, including a new method for producing organisms or pathogens, such as viruses, such as the virus that causes the swine disease known as porcine reproductive and respiratory syndrome (PRRS).

More generally, the invention relates to the propagation of organisms or pathogens such as viruses, e.g., virulent or attenuated viruses, using cotton rat lung cells or the cells or the cell line according to the invention (e.g., deposited cells or cell line or cells or cell line having identifying characteristics thereof) for the production of organisms or pathogens such as viruses, e.g., virulent or attenuated viruses, such as organisms or pathogens e.g., viruses, that do not normally have rodents or rats or the cotton rat or the cotton rat lung cell as a natural host, or RNA viruses, for instance positive-strand single stranded RNA viruses, like viruses of the Order Nidovirales, for example, arteviruses or viruses in the Arteriviridae family, e.g., lactate dehydrogenase elevating virus (LDV), equine arteritis virus (EAV), simian hemorrhagic fever virus (SHFV), and PRRS virus (whose vector is typically arthropods); viruses in the family Coronaviridae, e.g., coronaviruses such as infectious bronchitis virus, canine coronavirus, feline coronavirus, human coronavirus 229E, porcine epidemic diarrhea virus, transmissible gastroenteritis virus, porcine transmissible gastroenteritis virus, porcine respiratory virus, bovine coronavirus, human coronavirus OC43, murine hepatitis virus, porcine hemagglutinating encephalomyelitis virus, rat coronavirus, sialodacryoadenitis virus, avian infectious bronchitis virus, turkey coronavirus, rabbit coronavirus (also viruses whose vector is typically arthropods), and Toroviruses such as equine torovirus, porcine torovirus, human torovirus, bovine torovirus.

Viruses advantageously propagated using cotton rat lung cells or the cells or cell line according to the invention include Canine Parainfluenza (CPI), e.g., CPI type 2 (CPI-2), adenovirus, such as canine adenovirus (CAV) e.g., canine adenovirus type 2 (CAV-2), porcine adenovirus (PAV), e.g., porcine adenovirus type 3 and type 5 (PAV-3), bovine herpesvirus, e.g., bovine herpesvirus type 1 (responsible for infectious bovine rhinotracheitis (IBR)), equine herpesvirus (EHV), e.g. type 1 (EHV-1) or type 4 (EHV-4), bovine rotavirus (BRV), bovine parainfluenza virus type 3 (PI-3), enteric and respiratory bovine coronavirus (BCV), porcine reproductive and respiratory syndrome virus (PRRSV).

More advantageously the virus is the PRRS virus.

And in rather advantageous embodiments, the cotton rat lung cells or cell line is that which has been deposited with the ATCC as PTA-3930 or a cotton rat lung cell or cell line having all the identifying characteristics of ATCC PTA-3930 or a cotton rat lung cell or cell line produced by culturing cotton rat lung cells up to at least 10, e.g., up to at least 21 or 76 or 100 passages such as 10 or more or 21 or more or 76 or more passages, e.g., at least 10 or 21 or 76 passages and advantageously up to (and including) 100 passages, and establishing a cell line such that the cotton rat lung cells are essentially epithelial cells and the morphologic characteristics are maintained along the passages.

The invention accordingly relates to such cells or cell line, as well as all uses thereof.

Viruses propagated using cotton rat lung cells or cells or the cell line according to the invention are useful for the preparation of immunogenic compositions and vaccines against diseases caused by the viruses, such as PRRSV. Likewise, organisms or other pathogens propagated using the cotton rat lung cells or cells or the cell line according to the invention are useful for the preparation of immunogenic and vaccine compositions against such other pathogens or organisms.

This invention also relates to the use of viruses grown by passage on cells according to the invention, for instance, to provide attenuated, inactivated and sub-unit immunogenic compositions and vaccines; and thus, the invention relates to such attenuated, inactivated or sub-unit immunogenic compositions and vaccines.

BACKGROUND

Porcine reproductive and respiratory syndrome (PRRS) was first described in North Carolina (USA) in 1987. This swine disease was defined at that moment as "Mystery Swine Disease" or MSD, and was later known as "Swine Infertility and Respiratory Syndrome", or SIRS. It next appeared in Central Europe in 1990. At the beginning, in Europe, the disease was named "Porcine Epidemic Abortion and Respiratory Syndrome" or PEARS, and, finally, "Porcine Reproductive and Respiratory Syndrome" or PRRS which became the worldwide accepted denomination.

PRRS virus is an enveloped, single-stranded RNA virus, isolated for the first time in The Netherlands, and named as Lelystad virus. It has been classified as a member of the Arteriviridae family. Viruses of the Arteriviridae family are in the Order Nidovirales. Other viruses in the Order Nidovirales are viruses in the family Coronaviridae such as coronaviruses and toroviruses.

PRRS has been described in WO92/21375. An isolate as deposited with the Collection Nationale de Culture de Microorganismes (CNCM) of Institut Pasteur, Paris, France, under the accession number I-1102. A North American type was also isolated (WO93/03760) and the virus was deposited with the American Type Culture Collection (ATCC) under the accession number VR-2332.

In sows, the disease PRRS is characterized by reproductive disorders and respiratory symptoms. The target cells for the PRRS viruses are the macrophage cells.

One of the problems that has hindered the obtaining of immunological products against PRRS virus is the limited availability of stable substrates for virus replication.

PRRS virus could only be amplified in porcine alveolar macrophage (PAM) cultures (Wensvoort G., et al. in The Vet. Quart. 13:121-130, 1991). The need to use disease-free pigs of a certain age for the obtaining of these macrophages implied several drawbacks. Moreover, susceptibility to viral infection was not guaranteed in the recovered PAM, because cell substrates derived from different animals are always variable. This posed a major drawback in the production of antigen batches of constant and homogenous quality, and each batch needed to be evaluated in order to determine its susceptibility.

There has been research for other cell substrates. Thus, in U.S. Pat. No. 5,476,778, 15 cell lines obtained from various species (e.g., bovine, canine, feline, human, porcine, simian) and from various tissues (e.g.: kidney, lung, testicle) were tested for the culture of PRRS virus. Only one type (MA-104 cells) of 15 cell lines permits the growth of PRRS virus.

Monkey kidney cell lines (for example VERO, MA-104, MARC-145, see respectively U.S. Pat. No. 5,476,778 and WO98/00165) are used for the culture and attenuation of PRRS virus. But PRRS virus titers on these cells are low and therefore the cost of production is high.

Although inactivated and attenuated PRRS vaccines are now commercially available, it would be of great value to have alternative cell substrates to produce PRRS virus, e.g., for the production of vaccines or immunogenic compositions. And, more generally it would be of great value to have alternative cell substrates to produce pathogens, such as viruses, for instance, RNA viruses, for example, positive-strand single stranded RNA viruses, like viruses of the Order Nidovirales, such as arteviruses or viruses in the Arteriviridae family and viruses in the family Coronaviridae, e.g., for the production of vaccines or immunogenic compositions.

Moreover, it would be advantageous to provide a new cotton rat lung cell line.

SUMMARY OF THE INVENTION

The present invention is based on the finding that although rodents are not natural hosts for PRRS virus, lung cells from the cotton rat are permissive to PRRS virus growth or propagation. Further a new cell line derived from cotton rat lung tissue has been produced and deposited.

The present invention also is based on the finding that lung cells from the cotton rat are also permissive to others virus growth or propagation, which viruses are not a natural pathogens of rodents. These viruses include canine parainfluenza virus type 2 (CPI-2), canine adenovirus type 2 (CAV-2), equine herpesvirus type 1 (EHV-1), equine herpesvirus type 4 (EHV-4), bovine rotavirus (BRV) and bovine coronavirus (BCV).

The present invention, more generally, involves the use of cotton rat lung cells or cells or the cell line according to the invention to propagate organisms or pathogens like viruses e.g., virulent or attenuated viruses, such as viruses that do not normally have rodents or rats or the cotton rat or cotton rat lung cells as a natural host or viruses of the Order Nidovirales, for example, arteviruses or viruses in the Arteriviridae family, e.g., lactate dehydrogenase elevating virus (LDV), equine arteritis virus (EAV), simian hemorrhagic fever virus (SHFV), and PRRS virus (whose vector is typically arthropods); viruses in the family Coronaviridae, e.g., coronaviruses such as infectious bronchitis virus, canine coronavirus, feline coronavirus, human coronavirus 229E, porcine epidemic diarrhea virus, transmissible gastroenteritis virus, porcine transmissible gastroenteritis virus, porcine respiratory virus, bovine coronavirus, human coronavirus OC43, murine hepatitis virus, porcine hemagglutinating encephalomyelitis virus, rat coronavirus, sialodacryoadenitis virus, avian infectious bronchitis virus, turkey coronavirus, rabbit coronavirus (also viruses whose vector is typically arthropods), and Toroviruses such as equine torovirus, porcine torovirus, human torovirus, bovine torovirus.

Viruses advantageously propagated using cotton rat lung cells or the cells or cell line according to the invention include Canine Parainfluenza (CPI), e.g., CPI type 2 (CPI-2), adenovirus, such as canine adenovirus (CAV) e.g., canine adenovirus type 2 (CAV-2), porcine adenovirus (PAV), e.g., porcine adenovirus type 3 (PAV-3), bovine herpesvirus, e.g., bovine herpesvirus type 1 (responsible for infectious bovine rhinotracheitis (IBR)), equine herpesvirus (EHV), e.g. type 1 (EHV-1) or type 4 (EHV-4), bovine rotavirus (BRV), bovine parainfluenza virus type 3 (PI-3 or bPI-3), bovine coronavirus (BCV), and porcine reproductive and respiratory syndrome virus (PRRSV). More advantageously the virus is the PRRS virus. Accordingly, the invention relates to the propagation or culturing or growing of such viruses.

Some viruses may grow on lung cells from the Cotton Rat such as bovine herpesvirus type 1 (BHV-1) (see Papp Z. et al., J. Gen. Virol., 1997, 78, 2933-2943, e.g. p. 2935), bovine parainfluenza virus type 3 (bPI-3) (see Breker-Klassen M. M. et al., J. Virol., 1995, 69(7), 4308-4315), and porcine adenovirus type 3 (PAV-3) (see PCT patent application WO-A3-99/53047). These documents fail to describe or suggest the use of such cells and viruses produced thereon for the preparation of inactivated, attenuated or sub-unit immunogenic compositions or vaccines and their administration to animals and methods of immunization or vaccination.

The invention also involves the cotton rat lung cells or cell line is that which has been deposited with the ATCC as PTA-3930 or a cotton rat lung cell or cell line having all the identifying characteristics of ATCC PTA-3930 or a cotton rat lung cell or cell line produced by culturing cotton rat lung cells up to at least 10 or 21 or 76 passages such as 10 or more or 21 or more or 76 or more passages, e.g., at least 10 or 21 or 76 passages and advantageously up to and including 100 passages, and establishing a cell line such that the cotton rat lung cells are essentially epithelial cells and the morphologic characteristics are maintained along the passages.

The present invention advantageously involves the use Cotton Rat lung cells (CRL cells), e.g., cell lines made from these cells, for the propagation of virulent or attenuated PRRS virus.

The present invention advantageously also involves the use of CRL cells, e.g., cells or cell lines made from these cells such as cells or cell lines of the invention (e.g., the deposited cell line or cells having characteristics thereof), for the propagation of organisms or pathogens such as viruses, e.g., virulent or attenuated virus, such as CPI-2, CAV-2, EHV-1, EHV-4, BRV, BCV.

Thus, the invention comprehends a method for culturing or propagating a virus, such as PRRSV, CPI-2, CAV-2, PAV-5, EHV-1, EHV-4, BRV, BCV, LDV, EAV, SHFV, infectious bronchitis virus, canine coronavirus, feline coronavirus, human coronavirus 229E, porcine epidemic diarrhea virus, transmissible gastroenteritis virus, porcine transmissible gastroenteritis virus, porcine respiratory virus, bovine coronavirus, human coronavirus OC43, murine hepatitis virus, porcine hemagglutinating encephalomyelitis virus, rat coronavirus, sialodacryoadenitis virus, avian infectious bronchitis virus, turkey coronavirus, rabbit coronavirus, equine torovirus, porcine torovirus, human torovirus, bovine torovirus, comprising contacting the virus cotton rat lung cells under conditions suitable for culturing or propagating. The method can further include harvesting the resultant virus. For the preparation of an immunogenic or immunological or vaccine composition, the virus optionally can be inactivated and/ or have protein(s) or antigen(s) or epitope(s) isolated therefrom (for inactivated or subunit compositions) and the virus or the subunit can be admixed with a suitable carrier or diluent and/or adjuvant, e.g., a veterinarily acceptable or phamaceutically acceptable carrier or diluent and/or adjuvant.

The terms "immunogenic composition" and "immunological composition" and "immunogenic or immunological composition" cover any composition that elicits an immune response against the targeted pathogen; for instance, after administration or injection into the animal (such as porcine), elicits an immune response against the targeted pathogen (e.g., PRRS). The terms "vaccinal composition" and "vaccine" and "vaccine composition" covers any composition that induces a protective immune response against the targeted pathogen or which efficaciously protects against the pathogen; for instance, after administration or injection into the animal (e.g., porcine), elicits a protective immune response against the targeted pathogen or provides efficacious protection against the pathogen (e.g., PRRS). A subunit of a pathogen, e.g., virus, an antigen or immunogen or epitope isolated from the pathogen, e.g., virus; and, a subunit composition comprises or consists essentially of one or more antigens, immunogens or epitopes isolated from the pathogen, e.g., virus.

The present invention also provides cultures of an organism or pathogen, e.g., virus, such as a virus that does not normally have rodents or rats or the cotton rat or cotton rat lung cell as it natural host, for example, PRRSV, LDV, EAV, SHFV, infectious bronchitis virus, canine coronavirus, feline coronavirus, human coronavirus 229E, porcine epidemic diarrhea virus, transmissible gastroenteritis virus, porcine transmissible gastroenteritis virus, porcine respiratory virus, bovine coronavirus, human coronavirus OC43, murine hepatitis virus, porcine hemagglutinating encephalomyelitis virus, rat coronavirus, sialodacryoadenitis virus, avian infectious bronchitis virus, turkey coronavirus, rabbit coronavirus, equine torovirus, porcine torovirus, human torovirus, bovine torovirus, CPI-2, CAV-2, PAV-5, EHV-1, EHV-4, BRV or BCV, advantageously PRRS virus, CPI-2, CAV-2, EHV-1, EHV-4, BRV or BCV, obtained from culturing or propagating on cotton rat lung cells or the cells or cell line of the invention, e.g., inactivated, attenuated and sub-unit cultures or preparations.

Such cultures are different from previous cultures as they can have be free of contaminants from cultures propagated on different cells and can have different titres from cultures propagated on different cells. For instance, consider again PRRS virus amplified in porcine cells; cultures thereof are susceptible to containing contaminants from porcine cells, and PRRSV cultured on CRL cells are likely to not contain contaminants found in porcine cells. This analysis can be extended to cultures of PRRSV and other viruses cultured on other cells that have been used to propagate PRRSV and other viruses in comparison to cultures of viruses cultured on CRL cells as in the instant invention, such that it is clear that cultures of the instant invention are different than prior cultures.

The present invention also comprehend immunogenic compositions and vaccines against PRRS disease or PRRSV that can be obtained from PRRS virus culture according to the invention, advantageously live attenuated immunogenic compositions and vaccines, inactivated immunogenic compositions and vaccines and sub-unit immunogenic compositions and vaccines.

The present invention also comprehends immunogenic compositions and vaccines against other pathogens or organisms cultured or propagated on CRL cells or the cell line or cells of the invention, e.g., live attenuated, inactivated or subunit compositions, e.g., vaccines. These immunogenic compositions or vaccines can be against any organism or pathogen or virus grown, cultured, propagated, or the like on CRL cells or the cell line or cells of the invention, for instance, such immunogenic or vaccine compositions against any of the herein mentioned viruses or organims or pathogens, such as CPI-2, CAV-2, BHV-1, EHV-1, EHV-4, BRV, bPI-3 or BCV.

The invention comprehends kits containing cells and virus or organism or pathogen to culture thereon, advantageously in separate containers; and, even more advantageously, the separate containers are in the same packaging; and, optionally the kit includes instructions for culturing, growing, nurturing the cells and/or virus, with the instructions optionally including instructions for harvesting and/or inactivating virus and/or isolating a subunit antigen or immunogen or epitope.

The invention further comprehends combination compositions; for instance, compositions comprising one or more inventive vaccines or immunogenic compositions, or an inventive vaccine or immunogenic composition in combination with another vaccine or immunogenic composition or active component (e.g., inactivated or attenuated virus or pathogen or organism or subunit antigen or immunogen or protein or epitope thereof).

Thus, for example, the invention comprehends immunogenic compositions and vaccines against porcine disease comprising a mixture of PRRS and PAV-3 virus cultures according to the invention, such as live attenuated immunogenic compositions and vaccines, inactivated immunogenic compositions and vaccines or sub-unit immunogenic compositions and vaccines. The PAV-3 can be also a recombinant PAV-3 that contains one or more nucleic acid sequence(s) encoding, and which expresses, one or more foreign or heterologous or exogenous immunogen(s), antigen(s) or epitope(s) (foreign, heterologous or exogenous as to the adenovirus). Mention is made of WO99/53047, WO99/08706, WO01/83737 and WO00/47756 as to examples of recombinant porcine adenovirus vectors that can be used in the practice of the invention.

Another example is that the invention comprehends immunogenic compositions and vaccines against canine disease that comprise a mixture of CPI-2 and CAV-2 virus cultures according to the invention, such as live attenuated immunogenic compositions and vaccines, inactivated immunogenic compositions vaccines or sub-unit immunogenic compositions and vaccines. The CAV-2 can be also a recombinant CAV-2 that contains one or more nucleic acid sequence(s) encoding, and which expresses, one or more foreign or heterologous or exogenous immunogen(s), antigen(s) or epitope(s) (foreign, heterologous or exogenous as to the adenovirus). Mention is made of U.S. Pat. No. 6,090,393 as to examples of recombinant canine adenoviruses that can be used in the practice of the invention.

A further example is that the invention comprehends immunogenic compositions and vaccines against bovine disease that comprise a mixture of at least two or at least three or all four virus cultures according to the invention comprising BHV-1, BRV, bPI-3 and/or BCV, e.g., BHV-1+BRV, BHV-1+BRV+bPI-3, BHV-1+BRV+bPI-3+BCV, BRV+bPI-3, BRV+bPI-3+BCV, bPI-3+BCV, BHV+bP-3, BHV+bPI-3+BCV, BHV-1+BCV, BRV+BCV, such as live attenuated immunogenic compositions and vaccines, inactivated immunogenic compositions and vaccines or sub-unit immunogenic compositions and vaccines. Iimmunogenic compositions and vaccines against bovine respiratory disease that comprise a mixture of at least two virus cultures according to the invention comprising BHV-1 and bPI-3, and immunogenic compositions and vaccines against bovine enteric disease that comprise a mixture of at least two virus cultures according to the invention comprising BCV and BRV are considered advantageous.

And, a yet further example of combination compositions according to the invention are the immunogenic compositions and vaccines against equine disease that comprise a mixture of EHV-1 and EHV-4 virus cultures according to the invention, such as live attenuated immunogenic compositions and vaccines, inactivated immunogenic compositions and vaccines or sub-unit immunogenic compositions and vaccines.

The invention comprehends preparing such combination compositions; for instance by admixing the active components, advantageously together and with a carrier or diluent and/or adjuvant.

The invention also comprehends a kit for preparing the combination immunogenic or vaccine compositions of the invention; for instance, such a kit that comprises (a) an organism, pathogen or virus or antigen or epitope thereof (advantageously a virus as mentioned herein) and (b) an organism, pathogen or virus or immunogen, antigen or epitope thereof (advantageously a virus or immunogen, antigen or epitope thereof, but other pathogens as herein mentioned are also contemplated) that is different than (a), in separate containers, optionally in the same package, and optionally with instructions for admixture and/or administration.

The invention further comprehends methods for inducing an immune response by administering to a host, such as a host susceptible to a disease caused by a pathogen or organism or virus propagated on a cotton rat lung cell or cell line, e.g., a cotton rat lung cell or cell line of the invention, e.g., a virus as herein mentioned, an immunogenic or vaccine composition of the invention comprising such an inactivated or attenuated pathogen or organism or virus or an antigen or immunogen or epitope thereof in an amount sufficient to induce the immune response.

Thus, the present invention provides methods for immunization or vaccination or inducing an immune response against PRRS disease or virus using inventive an immunogenic composition and/or vaccine, e.g., administering the immunogenic or vaccine composition to a host, e.g., porcine, in an amount sufficient to elicit a suitable immune response. And the invention further provides methods for immunization or vaccination or inducing an immune response against CPI-2, CAV-2, BHV-1, EHV-1, EHV-4, BRV, bPI-3 or BCV disease or virus using an immunogenic composition and/or vaccines of the invention, administering the immunogenic or vaccine composition to a host, e.g., a natural host of the virus, in an amount sufficient to elicit a suitable immune response.

The present invention, e.g., when cocktail or combination compositions are employed, involves methods of immunization or vaccination or of eliciting an immune response in a host animal against two or more different antigens, epitopes or pathogens or organisms or viruses, such as in a porcine against PRRS and PAV-3 disease comprising administering an effective amount for eliciting the response of the immunogenic composition(s) and/or vaccine(s) of the invention. (The "(s)" indication is used as the method also can be practiced by sequentially administering compositions or vaccines of the invention.) Likewise, as a further example, the invention involves methods of immunization or vaccination or eliciting an immune response in a canine against CPI-2 and CAV-2 disease or virus using or administering an effective amount of immunogenic composition(s) and/or vaccine(s) of the invention. Similarly, the invention provides methods of immunization or vaccination or of eliciting an immune response in a bovine against at least two or at least three or at least four bovine diseases or viruses using or administering an effective amount of the immunogenic composition(s) and/or vaccine(s) of the invention. Further the invention involves methods of immunization or vaccination or of eliciting an immune response in a bovine against BHV-1 and bPI-3 disease or virus using or administering immunogenic composition(s) and/or vaccine(s) of the invention. The invention also involves methods of immunization or vaccination or of eliciting an immune response in a bovine against BCV and BRV disease or virus using or administering immunogenic composition(s) and/or vaccine(s) of the invention. And, the invention involves methods of immunization or vaccination or of eliciting an immune response in an equine against EHV-1 and EHV-4 disease or virus using or administering immunogenic composition(s) and/or vaccine(s) of the invention.

It is noted that in this disclosure and particularly in the claims, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DETAILED DESCRIPTION

The inventors have developed a method for viral production or propagation which uses Cotton Rat lung cells, as well as a new cell line; and the propagation or production or culturing or growing of organisms or pathogens or viruses on such cells.

Lungs were collected from cotton rats and submitted to an enzymatic digestion (e.g. with trypsin and/or collagenase). Supernatant containing disassociated cells is collected and cultured for example as a monolayer or in suspension. Advantageously cells are cultured as a monolayer for example in Minimum Essential Medium (MEM) supplemented with fetal bovine serum (FBS) and/or lactalbumin hydrosylate (LAH). Advantageously the culture medium may contain antibiotics, for example gentamycin, streptomycin and/or penicillin.

PRRS virus was cultured on such a lung cell culture. PAV-3, CPI-2, CAV-2, BHV-1, EHV-1, EHV-4, BRV, bPI-3 or BCV viruses are also cultured on such a lung cell culture.

The cell culture may advantageously result from several passages of these cells. Advantageously, the passages of these cells allows one to produce cell lines that are useful, for instance, for PRRS virus propagation. For example, the cells can be subjected to at least 10 passages, e.g. 10 to 100 passages. Advantageously these cell lines are durable in the absence of fetal bovine serum (FBS), although the establishment of the monolayer requires some FBS or another appropriate cell growth factor.

Another advantage of the culture of CRL cells according to the invention is that, a culture of cells may persist for at least a month as a healthy monolayer or suspension without requiring replacement of spent media or additional nutritional supplementation. This hardiness has conferred the advantage of multiple virus harvests from the same culture of cells without necessitating start-up time (culture establishment) and cell stock consumption. It is thus possible to have multiple viral harvests from the same cell culture. In one embodiment the culture process comprises two or more harvests of the virus, with or without viral re-inoculation and/or addition of fresh culture media. Advantageously after each harvest fresh culture media is added to the cell culture.

Following this procedure, Cotton Rat lung cells have been cultured up to 76 passages and established as a cell line. These Cotton Rat lung cells are essentially epithelial cells and the morphologic characteristics are maintained along the passages. The passage 21 has been deposited on Dec. 18, 2001, under the terms of the Budapest Treaty with the American Type Culture Collection, 10801 University Blvd., Manassas, Va. 20110-2209, and has been assigned the accession number ATCC PTA-3930.

In an embodiment, the present invention involves the use of Cotton Rat epithelial lung cells, epithelial cell lines derived therefrom, such as the cell line PTA-3930 or a cell line having the identifying characteristics thereof, for the production of virulent or attenuated PRRS virus. In additional embodiments, the present invention involves the use of Cotton Rat epithelial lung cells, epithelial cell lines derived therefrom, such as the cell line PTA-3930 or a cell line having the identifying characteristics thereof, for the production of virulent or attenuated CPI-2, CAV-2, EHV-1, EHV-4, BRV or BCV virus. In further embodiments, the present invention involves the use of cell line PTA-3930 or a cell line having the identifying characteristics thereof for the production of virulent or attenuated BHV-1 or bPI-3 virus. The cell line or a cell line having the identifying characteristics thereof can also be used with respect to other herein mentioned viruses.

Another aspect of the invention is thus a method of producing PRRS virus, comprising culturing PRRS virus on a Cotton Rat lung cell culture, comprising epithelial cells, advantageously on a Cotton Rat lung cell line. For example, viral production is done on the cell line PTA-3930 or a cell line having the identifying characteristics thereof. This method of producing viruses may also be used for CPI-2, CAV-2, BHV-1, EHV-1, EHV-4, BRV, bPI-3 and BCV viruses, as well as for other viruses herein mentioned.

The virus can be a virulent virus or an attenuated virus.

The production of virus comprises the steps of inoculating and propagating the virus on such cells. Before inoculation, the cells according to the invention can be grown in a suitable culture medium, for example MEM medium supplemented with FBS or another appropriate cell growth factor. The cell culture is advantageously done at a temperature between 35 and 39° C., advantageously at around 37° C. Advantageously the cell culture is a monolayer. Alternatively the cell culture is a suspension. In general the virus is inoculated when the cells grown in monolayer are confluent. Extracellular virus can be recovered directly with the supernatant. Intracellular virus can be recovered after appropriate disruption of the cells, for example by freeze/thaw or sonication. In case of cell cultures in suspension, the virus can be recovered, e.g., after filtration of the filtrate. The virus can be recovered 2 to 15 days, such as 3 to 7 days, more advantageously 5 to 7 days post-inoculation. The production of the virus is done according to the general knowledge of the man skilled in the art concerning viral production. Virus crude culture is obtained at this stage.

The culture media used in this invention may be supplemented with antibiotics.

If necessary the virus, e.g., PRRS virus, is adapted to the growth on the cells according to the invention. Adaptation can be made by co-cultures on cells according to the invention and monkey kidney cells such as MA-104. The adaptation is done as it is well known by serial passages on co-cultures with incrementally increasing amount of cells according to the invention. This adaptation may also be done for CPI-2, CAV-2, BHV-1, EHV-1, EHV-4, BRV, bPI-3 or BCV viruses, as well as other viruses herein mentioned.

The crude culture may be concentrated and/or purified.

Concentration can be performed by any conventional method known by a skilled person in the art, for example by selective precipitation or by ultrafiltration. Purification can be performed by any conventional method known by a person skilled in the art, for example ultracentrifugation or chromatography methods, e.g., gel-filtration. Virus concentrated cultures, purified cultures or concentrated and purified cultures are obtained at this stage.

In another aspect of the invention, the virus cultures according to the invention (crude, concentrated, purified or concentrated and purified) can be inactivated by using any conventional method, for example thermal and/or chemical method. An advantageous method is chemical inactivation, for instance, using beta-propiolactone, formalin, ethylenimine or a derivative thereof such as binary ethylenimine (BEI) and combinations of these inactivating compounds. Inactivated PRRS virus cultures are obtained at this stage.

In another aspect of the invention, immunogenic fractions like glycoproteins or proteins can be extracted from the virus present in the virus cultures according to the invention (crude, concentrated, purified or concentrated and purified, optionally inactivated). The extraction of immunogenic fractions of the virus is done according to the general knowledge of a skilled person in the art. Sub-unit virus preparations are obtained at this stage.

Other aspects of the invention are thus the herein described virus crude cultures, concentrated cultures, purified cultures, concentrated and purified cultures, inactivated cultures, sub-unit preparations.

In an advantageous embodiment of the invention, the virulent virus can be attenuated by a sufficient number of passages on cells according to the invention. A person skilled in the art is able to determine by routine experimentation the number of passages sufficient for attenuation of the virus. Attenuated virus preparation is obtained.

It is also an object of this invention to provide immunogenic compositions and vaccines to prevent infection with the virus. These immunogenic compositions or vaccines comprise at least one culture or preparation as described herein.

The term of "immunogenic composition" covers herein any composition able, once it has been administered to an animal, e.g., porcine, to elicit an immune response against the virus or antigen or immunogen or epitope. The term of "vaccine" covers herein any composition able, once it has been administered to the animal, e.g., porcine, to induce a protective immune response against the virus, or to efficaciously protect the animal against said virus.

Immunogenic compositions or vaccines according to the invention can include the virus culture or preparation or antigen or immunogen or epitope of the virus, and at least one immunogen, antigen or epitope of another pathogen or another pathogen (e.g., inactivated or attenuated pathogen). Such an immunogen, antigen or epitope may e.g. be of bacterial, or parasitic or viral origin or an inactivated or attenuated form of the pathogen. The invention also comprehends kits to prepare these combination compositions, as well as methods for making these combination compositions and the use of the components of these combination compositions to prepare the combination compositions. Accordingly, the invention involves a kit for preparing the combination immunogenic or vaccine compositions of the invention; for instance, such a kit that comprises (a) an organism, pathogen or virus or antigen or epitope thereof (advantageously a virus as mentioned herein) and (b) an organism, pathogen or virus or immunogen, antigen or epitope thereof (advantageously a virus or immunogen, antigen or epitope thereof, but other pathogens as herein mentioned are also contemplated) that is different than (a), in separate containers, optionally in the same package, and optionally with instructions for admixture and/or administration.

Immunogenic compositions and/or vaccines according to the invention can include PRRS virus culture or preparation (e.g., inactivated or attenuated PRRSV or an immunogen or antigen or epitope thereof), and at least one immunogen, antigen or epitope of another porcine pathogen (including without limitation the pathogen in inactivated or attenuated form). This pathogen can be selected from the group including but not limited to pseudorabies virus, porcine influenza virus, porcine parvovirus, transmissible gastro-enteritis virus (coronavirus), porcine circovirus such as porcine circovirus type 2, rotavirus, porcine adenovirus type 3, *Escherichia coli, Erysipelothrix rhusiopathiae, Bordetella bronchiseptica, Clostridium* spp., *Salmonella* spp., *Haemophilus parasuis, Pasteurella multocida, Streptococcus suis, Mycoplasma hyopneumoniae* and *Actinobacillus pleuropneumoniae.* Advantageously immunogenic compositions and vaccines according to the invention can include a PRRS virus culture or preparation and PAV-3 viruses grown and propagated on cells or cell lines according to the invention, e.g. on PTA-3930 cell line or a cell line having all the identifying characteristics thereof. Immunogens of porcine pathogens can include pseudorabies virus gB, pseudorabies virus gC, pseudorabies virus gD, swine influenza HA, swine influenza NA, swine influenza NP, ORF4 of porcine reproductive and respiratory syndrome virus, ORF7 of porcine reproductive and respiratory syndrome virus, ORF5 of PRRSV, PRRSV ORF3, PRRSV ORF6, PRRSV open reading frames 5 (ORF5) and 6 (ORF6), PRRSV open reading frames 5 (ORF5) and 3 (ORF3) and 6 (ORF6), Hog Cholera Virus E1, Hog Cholera Virus E2 gene, parvovirus VP2, porcine circovirus type 2 ORF1, or porcine circovirus type 2 ORF2. Reference is made to U.S. Pat. Nos. 6,517,843, 6,497,883, 6,391,314, 6,379,676, 6,217,883, 6,207,165 and U.S. patent publication 2003003112 and WO99/53047, WO99/08706, WO01/83737, and WO00/47756 for immunogens of porcine pathogens, nucleic acid molecules coding therefor and constructs expressing the same. Thus, the invention also involves methods for making these compositions, as well as kits therefor.

Immunogenic compositions and vaccines according to the invention can include CPI-2 and/or CAV-2 virus culture or preparation (e.g., inactivated or attenuated CPI-2 and/or CAV-2 or an immunogen or antigen or epitope thereof), and at least one immunogen, antigen or eptiope of another canine pathogen (including without limitation the pathogen in inactivated or attenuated form). This pathogen can be selected from the group including but not limited to canine distemper virus, canine parvovirus, canine coronavirus, canine herpesvirus, Lyme disease agent, *Borrelia burgdorferi* and rabies virus. Advantageously immunogenic compositions and vaccines according to the invention include a CPI-2 virus culture or preparation and/or a CAV-2 virus culture or preparation according to the invention. CPI-2 immunogens can be CPI-2 F and/or HN. See also U.S. Pat. Nos. 5,616,326, 6,090,393, 6,159,477, 6,228,846 regarding immunogens of canine pathogens and nucleic acid molecules coding therefor and consctructs that express the same. Thus, the invention also involves methods for making these compositions, as well as kits therefor.

Immunogenic compositions and vaccines according to the invention can include BHV-1, BRV, bPI-3 and/or BCV virus culture or preparation (e.g., inactivated or attenuated BHV-1, BRV, bPI-3 and/or BCV or an immunogen or antigen or epitope thereof), and at least one immunogen, antigen or epitope of another bovine pathogen (including without limitation the pathogen in inactivated or attenuated form). This pathogen can be selected from the group including but not limited to bovine respiratory syncytial virus and bovine viral diarrhea virus. Advantageously immunogenic compositions and vaccines according to the invention include at least two virus cultures or preparations according to the invention comprising BHV-1, BRV, bPI-3 or BCV. BRSV immunogens can be BRSV F or G or N, such as BRSV F and/or G or N and/or G. BHV-1 immunogens can be gB and/or gC and/or gD. BVDV immunogens can be E0 the protein (gp48) and/or the E2 protein (gp53). The BVDV can be type 1 and/or type 2. The bPI-3 immunogens can be bPI-3 F and/or HN. See also U.S. Pat. Nos. 6,451,770, 6,376,473, 6,224,878, regarding immunogens of bovine pathogens and nucleic acid molecules coding therefor and constructs that express the same. Thus, the invention also involves methods for making these compositions, as well as kits therefor.

Immunogenic compositions and vaccines according to the invention can include a EHV-1 and/or EHV-4 virus culture or preparation (e.g., inactivated or attenuated EHV-1 and/or EHV-4 or an immunogen or antigen or epitope thereof), and at least one immunogen, antigen or epitope of another equine pathogen (including without limitation the pathogen in inactivated or attenuated form). This pathogen can be selected from the group including but not limited to equine influenza virus, eastern encephalomyelitis virus (EEV), western encephalomyelitis virus (WEV), Venezuelan encephalomyelitis virus (VEV), Lyme disease agent, *Borrelia burgdorferi, Clostridium tetani, equine arteritis* virus (EAV) and rabies virus. Advantageously immunogenic compositions and vaccines according to the invention can include a EHV-1 virus culture or preparation and EHV-4 virus culture or preparation according to the invention. EHV glycoproteins can be gB, gD, gB+gD, gC, and gE. Reference is made to U.S. Pat. Nos. 6,207,166 and 6,368,603 for immunogens of equine pathogens and nucleic acid molecules coding therefor and consturcts that express the same. Thus, the invention also involves methods for making these compositions, as well as kits therefor.

An immunogenic composition or vaccine according to the invention that also comprises such an additional immunogenic component (additional immunogen, antigen or epitope) has the advantage that it induces an immune response or protection against several infections or maladies or causative agents thereof at the same time. This additional immunogenic component can be an attenuated or inactivated micro-organism, a recombinant construct or sub-units (e.g. proteins, glycoproteins, polypeptides, or epitopes). Epitope determination procedures, such as, generating overlapping peptide libraries (Hemmer B. et al., Immunology Today, 1998, 19 (4), 163-168), Pepscan (Geysen H. M. et al., Proc. Nat. Acad. Sci. USA, 1984, 81 (13), 3998-4002; Geysen H. M. et al., Proc. Nat. Acad. Sci. USA, 1985, 82 (1), 178-182; Van der Zee R. et al., Eur. J. Immunol., 1989, 19 (1), 43-47; Geysen H. M., Southeast Asian J. Trop. Med. Public Health, 1990, 21 (4), 523-533; Multipin Peptide Synthesis Kits de Chiron) and algorithms (De Groot A. et al., Nature Biotechnology, 1999, 17, 533-561), can be used in the practice of the invention, to determine epitopes of immunogens, antigens, polypeptides, glycoproteins and the like, without undue experimentation. From that information, one can construct nucleic acid molecules encoding such an epitope; and from that knowledge and knowledge in the art, one can construct vectors or constructs, e.g., recombinant viruses or vectors or plasmids that express immunogens, epitopes or antigens; all without undue experimentation.

The immunogenic compositions or the vaccine compositions further comprise a pharmaceutically or veterinarily acceptable excipient, diluent or vehicle, and optionally a stabilizer and/or an adjuvant. Suitable formulations will be apparent to any person skilled in the art. The formulations may be developed for any suitable route of administration.

The pharmaceutically acceptable vehicle may be water or saline.

The inactivated immunogenic compositions or inactivated vaccines advantageously comprise at least one adjuvant.

The live attenuated viruses may be freeze-dried, advantageously with a stabilizer. Freeze-drying can be done according to well-known standard freeze-drying procedures. The pharmaceutically acceptable stabilizers may be SPGA (sucrose phosphate glutamate albumine) (Bovarnik et al., J. Bacteriology, 1950, 59: 509), carbohydrates (e.g. sorbitol, mannitol, lactose, sucrose, glucose, dextran, trehalose), sodium glutamate (Tsvetkov T et al., Cryobiology 1983, 20(3): 318-23; Israeli E et al., Cryobiology 1993, 30(5): 519-23), proteins such as peptone, albumin or casein, protein containing agents such as skimmed milk (Mills C K et al., Cryobiology 1988, 25(2): 148-52; Wolff E et al., Cryobiology 1990, 27(5): 569-75), and buffers (e.g. phosphate buffer, alkaline metal phosphate buffer).

An adjuvant may be used to make soluble the freeze-dried preparations.

Examples of adjuvants are oil-in-water, water-in-oil-in-water emulsions based on mineral oil and/or vegetable oil and non ionic surfactants such as block co-polymers, Tween®, Span®. Other suitable adjuvants are for example vitamin E, saponins, Carbopol®, aluminium hydroxide, aluminium phosphate or aluminium oxide ("Vaccine Design, The subunit and adjuvant approach", Pharmaceutical Biotechnology, vol. 6, Edited by Michael F. Powell and Mark J. Newman, 1995, Plenum Press New York). Documents cited herein may also be consulted as to adjuvants, as well as for excipients diluents, carriers and vehicles.

Another aspect of the present invention is a method of immunization or a method of vaccination using the immunogenic compositions or the vaccine compositions according to the invention, respectively.

The method includes at least one administration to an animal of an efficient amount of the immunogenic composition or vaccine according to the invention. The animal may be male, female, pregnant female and newborn. This administration may be notably done by intramuscular (IM), intradermal (ID) or subcutaneous (SC) injection or via intranasal or oral administration. The immunogenic composition or the vaccine according to the invention can be administered by a syringe or a needleless apparatus (like for example Pigjet or Biojector (Bioject, Oregon, USA)).

For attenuated compositions the doses of the virus or organism or pathogen produced on the new cell culture may be between about $10^3$ and about $10^7$ $CCID_{50}$ (median Cell Culture Infectious Doses), advantageously between about $10^4$ and about $10^6$ $CCID_{50}$ and more advantageously about $10^5$ $CCID_{50}$. The volumes are from 0.2 to 2.0 ml, advantageously about 2.0 ml. One or more administrations can be done; e.g. with two injections at 2-4 weeks interval, and advantageously with a boost about 3 weeks after the first injection.

With inactivated compositions of the virus or organism or pathogen produced on the new cell culture, the animal may be administered approximately $10^4$-$10^9$ equivalent $CCID_{50}$ (titer before inactivation), advantageously approximately $10^5$-$10^8$ equivalent $CCID_{50}$ in a single dosage unit. The volume of one single dosage unit can be between 0.2 ml and 5.0 ml and advantageously between 0.5 ml and 2.0 ml and more advantageously about 2.0 ml. One or more administrations can be done; e.g. with two injections at 2-4 weeks interval, and advantageously with a boost about 3 weeks after the first injection.

With sub-unit compositions, e.g., from the virus or pathogen or organism produced on the new cell culture, the animal may be administered approximately 5 µg to 500 µg, advantageously 20 µg to 50 µg. The volumes are from 0.2 to 2.0 ml, advantageously about 2.0 ml. One or more administrations can be done; e.g. with two injections 2-4 weeks apart, and advantageously with a boost about 3 weeks after the first injection.

The compositions according to the invention may also be administered to other mammals, e.g. mice or laboratory animal, for instance to generate polyclonal antibodies, or to prepare hybridomas for monoclonal antibodies.

The invention will now be further described by way of the following non-limiting examples.

EXAMPLES

Example 1

Obtaining of Cotton Rat Lung (CRL) Cells

Upon excision from the euthanized animal, the lungs were placed into cell culture media containing minimum essential medium F-15 (MEM F-15, Hyclone, cat#SH30024.02) and gentamycin at 30 µg/ml. This media was supplemented with commercial antibiotic (penicillin and streptomycin) and antimycotic (amphotercin B) at a 2% v/v concentration. The lungs were digested at 37° C. in a 50 ml-conical centrifuge tube containing 25 ml of a solution of collagenase (Sigma, cat#L-0130) and trypsin (Sigma, cat#T-8003) at a concentration of 1 mg/ml and 1× strength (corresponds to a concentration of 2.5 mg/ml), respectively, in MEM F-15 containing gentamycin at 30 µg/ml. Following a 30-minute digestion, Fetal Bovine Serum (FBS) (BioWhittaker) was added at a final concentration of 10% v/v. Following dispersion of cells using a pipette and clarification, the supernatant containing disassociated cells was collected and plated into 25 $cm^2$ flasks with MEM F-15 medium containing gentamycin at 30 µg/ml and supplemented with FBS at a final concentration of 10% v/v.

Example 2

Culture of CRL Cells

A trypsin solution was used to rinse away residual FBS from a confluent monolayer of CRL cells obtained in example 1. Cells overlaid with 0.1% (1×) of a mixture of porcine trypsin with ethylene diamine tetraacetic acid (EDTA) (JRH Biosciences, cat#62244-79P) (3 ml for a 75 $cm^2$, 5 ml for a 150 $cm^2$ flask) were placed in an incubator at 37° C. and monitored closely until cell detachment is complete. Cells were dispersed using a pipette and 3 ml of cell suspension were collected. At that point, 1:4 of the cells collected were cultured with fresh cell culture media containing MEM F-15, gentamycin at a concentration of 30 µg/ml and FBS at a v/v concentration of 10%.

CRL cells were grown at 37° C. in incubators with 5% $CO_2$ partial pressure. A 1:4 split of a confluent monolayer was confluent in about 4 days, and a 1:8 split produced a confluent monolayer within about 7 days. This constitutes a passage.

Cells were then propagated from passage 2 to passage 76.

After addition of dimethyl sulfoxide (DMSO) cryoprotector, small banks were frozen at all passages up to 76. Banks are stored in liquid nitrogen.

CRL cells of passage 21 have been deposited with the American Type Culture Collection, under the accession number ATCC PTA-3930.

Example 3

Propagation of PRRS Virus on CRL Cells

Use was made of an attenuated PRRS virus known to propagate on monkey kidney cells.

The propagation of PRRS virus was done on a monolayer of CRL cells in a 75 cm² flask (T75 flask) with 50 ml of culture media containing MEM F-15, gentamycin at a concentration of 30 μg/ml and FBS at a v/v concentration of 10%. Before viral inoculation, the cells were incubated at 37° C. for 24 hours, until they were confluent. After inoculation with 1 ml of PRRS virus, the inoculated cells were incubated at 37° C. for 5-7 days. The viral growth was checked by indirect immunofluorescent antibody testing (IFA) and titration of the supernatant material. After freeze/thaw, the supernatant was harvested. This constitutes a crude culture of PRRS virus.

Indirect Immunofluorescent Antibody Testing (IFA)

For IFA, cells were trypsinized, dispersed, collected and resuspended in fresh MEM F-15 medium containing gentamycin (at 30 μg/ml) and supplemented with FBS to a concentration of 10% v/v. The cells were seeded in 96-well tissue culture treated plates at 100 μl/well and were allowed to grow to confluence overnight. Fourfold serial dilutions of the PRRS viruses were prepared. Then, either 100 μl or 200 μl of the diluted virus was loaded into each well in a row of the 96-well plate. The plate was placed in a 37° C., 5% $CO_2$ incubator for 7 days. Wells containing infected CRL cells were determined by indirect immunofluorescent antibody testing (IFA) with an anti-PRRS virus monoclonal antibody (SDOW 17, obtained from the USDA; Magar R. et al., Can J vet Res., 1995, 59(3): 232-4).

Characterization of PRRS Virus Grown on CRL Culture:

PRRS virus was titrated in a 96-well plate containing CRL cells. The titer was calculated using the Spearman-Karber method of 50% endpoint determination, and was reported on a per-ml basis. Results are expressed in $Log_{10}$ ($FAID_{50}$)/ml.

Titration result was 4.3 in $Log_{10}$ ($FAID_{50}$)/ml.

Example 4

Adaptation of PRRS Virus to Growth on CRL and Propagation

NADC 8 PRRS virus was adapted to grow on CRL cells. NADC 8 was obtained from the National Animal Disease Center (USDA).

The virus was sequentially propagated on co-cultures of CRL cells and MA-104 cells (African green monkey kidney cells, parent cell line of MARC-145) containing incrementally decreasing amount of MA-104 cells. Initially CRL cells were seeded at a 1:9 ratio with the MA-104 cells (20,000 cells/ml CRL:180,000 cells/ml MA-104) at 37° C., MEM F-15 with lactalbumin hydrosylate (LAH, at a v/v concentration of 0.1%), gentamycin at a concentration of 30 μg/ml and FBS at a v/v concentration of 10%. When these co-cultures were confluent, PRRS virus was inoculated (1 ml per T75 flask) without any medium replenishment. The viral growth was checked by indirect immunofluorescent antibody testing (IFA, as described in example 3) and titration of the supernatant material. The inoculated cells were incubated at 37° C. for 5-7 days. Passage includes a freeze/thaw, an harvest of the supernatant and a subsequent 1 ml inoculation of the successive co-culture T75 flask, i.e. about 10% of the harvested supernatant. This is repeated by passaging inoculum on co-cultures of CRL:MA-104 of ratios 2:8, 3:7, 4:6, 5:5, 6:4, 7:3, 8:2, and 9:1, respectively.

Finally in a T75 flask the virus was grown on a monolayer composed solely of CRL cells with 50 ml of culture media containing MEM F-15, gentamycin at a concentration of 30 μg/ml and FBS at a v/v concentration of 10% (so without LAH). The inoculated CRL cells were incubated at 37° C. for 5-7 days. After freeze/thaw, the supernatant was harvested. This constitutes a crude culture of PRRS virus.

The IFA showed that NADC 8 had infected CRL cells.

Characterization of PRRS Virus Grown on CRL Culture:

PRRS virus NADC 8 strain was titrated in a 96-well plate containing CRL cells. The culture was done as described before. The titer was calculated using the Spearman-Karber method of 50% endpoint determination, and was reported on a per-ml basis. Results are expressed in $Log_{10}$ ($FAID_{50}$)/ml.

Titration result was 4.12 in $Log_{10}$ ($FAID_{50}$)/ml.

Other viruses, such as other viruses of the Order Nidovirales, for example, arteviruses or viruses in the Arteriviridae family, e.g., lactate dehydrogenase elevating virus (LDV), equine arteritis virus (EAV), simian hemorrhagic fever virus (SHFV), viruses in the family Coronaviridae, e.g., coronaviruses such as infectious bronchitis virus, canine coronavirus, feline coronavirus, human coronavirus 229E, porcine epidemic diarrhea virus, transmissible gastroenteritis virus, porcine transmissible gastroenteritis virus, porcine respiratory virus, bovine coronavirus, human coronavirus OC43, murine hepatitis virus, porcine hemagglutinating encephalomyelitis virus, rat coronavirus, sialodacryoadenitis virus, avian infectious bronchitis virus, turkey coronavirus, rabbit coronavirus, Toroviruses such as equine torovirus, porcine torovirus, human torovirus, bovine torovirus, and other viruses whose host is not naturally a rodent or rat or the cotton rat, may be adapted to grow on cotton rat lung cells, advantageously the cotton rat lung cells or cell line of the invention (e.g., those deposited), employing techniques herein described or techniques analogous to those herein described with respect to PRRS.

Example 5

Method of Inactivation

PRRS virus propagated on CRL (example 3 or 4) are harvested. The viral suspension is sonicated at a temperature of about 5° C. The viral suspension is filtrated through a membrane of 50-100 μm porosity at about 5° C.

Beta-propiolactone is added to the viral suspension at the final concentration of 1/3000 (v/v). After homogenisation by stirring, the suspension is transferred into another sterile flask.

Inactivation is carried out under stirring for 24 hours at about 5° C. The pH is regulated at about 7.2 by 1M NaOH addition.

The inactivated viral suspension is concentrated by ultrafiltration of approximately 50 times. The concentrated viral suspension is stored at −40° C.

Example 6

Preparation of the Inactivated Vaccine in the Form of an Emulsion Based on Mineral Oil The vaccine is prepared with the inactivated PRRS virus obtained in example 5 (after thawing and dilution) and according to the following formula:

| | |
|---|---|
| suspension of inactivated PRRS virus: | 167 ml |
| oily phase: | 83 ml |

The oily phase 7% weight volume (w/v) of anhydromannitol oleate, 8% w/v of ethoxylated oleic acid (11 ethylen oxides) and 85% v/v of light liquid paraffin oil (according to European pharmacopoeia).

The aqueous phase and the oily phase are sterilized separately by filtration. The emulsion is prepared by mixing and homogenizing the ingredients with the aid of a Silverson turbine emulsifier.

One vaccine dose contains about $10^{7.5}$ $CCID_{50}$ (titer before inactivation). The volume of one vaccine dose is 2.0 ml for administration by the intramuscular route.

Example 7

Propagation of Viruses on CRL Cells

Viral stocks routinely used in assays as reference virus for which fluorescent antibody (FA) reagents were available were titrated using CRL cells. Because these reference viruses have been routinely titrated using standard cell lines, each has a known titer with various degrees of variation. Tenfold or fourfold dilutions of these reference viruses were used to inoculate CRL cells in a 96-well format using the standard method of titration for each virus. Following 7 days of incubation, the plates were fixed with acetone and stained with the appropriate FA reagents. Titers of the fluorescent-positive cultures were compared to the titers obtained from standard cell cultures. The results are presented below:

| Reference Virus | Titer/CRL | Titer/Standard cell line |
|---|---|---|
| Canine Parainfluenza type 2 (CPI-2) | 4.96 | 5.6 on MDCK cells |
| Canine Adenovirus type 2 (CAV-2) | 1.72 | 5.8 on MDCK cells |
| Bovine Herpesvirus type 1 (BHV-1) | 3.64 | 7.1 on MDBK cells |
| Equine Herpesvirus type 1 (EHV-1) | 5.74 | Titer not determined |
| Equine Herpesvirus type 4 (EHV-4) | 5.44 | 6.13 on Vero cells |
| Bovine Rotavirus (BRV) | 5.32 | 6.0 on MA-104 cells |
| Bovine Parainfluenza type 3 (bPI-3) | 6.46 | 7.0 on MDBK cells |
| Bovine Coronavirus (BCV) | 3.52 | 4.79 on MDBK cells |
| Porcine Reprod. & Respir. (PRRSV) | 5.22 | 5.34 on MARC-145 cells |

Virus titers are expressed in $\log_{10}$ of Cell Culture Infectious Dose 50 per milliliter ($\log_{10}$ $CCID_{50}$/ml)

Although in each case, the titers generated by the CRL-based assay were lower than that of the standard cell line, it must be emphasized that these viruses have not undergone the cell-adaptation process using CRL cells that the reference virus has with the standard cell line. This was only a test to detect any viral replication. In other words, with some effort, it is likely that the concentration of live virus grown on CRL cells could be improved to the extent that it would be equivalent or better than the concentration of virus grown on cell lines for which it was adapted. This is shown by the CRL-adapted PRRS (example 4) whose titers of the same serial dilution of virus were 5.22 and 5.34 ($\log_{10}$ $CCID_{50}$/ml) when CRL cells and MARC-145 cells (a sensitive subclone of MA-104 cells) were used, respectively. This difference in titer is negligible.

The invention is further described by the following numbered paragraphs:

1. A method of producing PRRS virus, wherein one prepares a Cotton Rat lung cell culture and one propagates the PRRS virus on this cell culture.

2. The method according to paragraph 1, wherein the cell culture comprises epithelial cells.

3. A method of producing PRRS virus, wherein one prepares a culture of cells from a Cotton Rat lung cell line and one propagates the PRRS virus on this culture.

4. The method according to paragraph 3, wherein the culture comprises epithelial cells.

5. A method of producing PRRS virus, wherein one prepares a Cotton Rat lung epithelial cell culture and one propagates the PRRS virus on this cell culture.

6. A method of producing PRRS virus, wherein one prepares a culture of cells from a Cotton Rat lung epithelial cell line and one propagates the PRRS virus on this cell line.

7. The method according to paragraph 3 or 6, wherein the cell line is the cell line deposited at the ATCC under the accession number PTA-3930, or a cotton rat lung cell line having all the identifying characteristics of the cell line deposited at the ATCC under the accession number PTA-3930.

8. The method according to paragraph 7, wherein the cell line is the cell line deposited at the ATCC under the accession number PTA-3930.

9. The method according to any one of paragraphs 1 to 8, wherein the PRRS virus is a virulent PRRS virus.

10. The method according to any one of paragraphs 1 to 8, wherein the PRRS virus is an attenuated PRRS virus.

11. The method according to any one of paragraphs 1 to 8, wherein one propagates the PRRS virus on the cells, and one recovers a crude culture of PRRS virus.

12. The method according to any one of paragraphs 1 to 8, wherein one propagates the PRRS virus on the cells, one recovers the PRRS virus giving rise to a crude culture of PRRS virus, and one subjects this crude culture to purification giving rise to a purified culture of PRRS virus.

13. The method according to any one of paragraphs 1 to 8, wherein one propagates the PRRS virus on the cells, one recovers the PRRS virus giving rise to a crude culture of PRRS virus, and one subjects this crude culture to concentration giving rise to a concentrated culture of PRRS virus.

14. The method according to any one of paragraphs 1 to 8, wherein one propagates the PRRS virus on the cells, one recovers the PRRS virus giving rise to a crude culture of PRRS virus, and one subjects this crude culture to concentration and purification giving rise to a concentrated and purified culture of PRRS virus.

15. The method according to paragraph 11, wherein one inactivates the crude culture.

16. The method according to paragraph 12, wherein one inactivates the purified culture.

17. The method according to paragraph 13, wherein one inactivates the concentrated culture.

19. The method according to paragraph 14, wherein one inactivates the concentrated and purified culture.

20. The method according to paragraph 15, 16, 17 or 18, wherein one inactivates the culture with a chemical agent.

21. The method according to paragraph 19, wherein the chemical agent is chosen among the group consisting of beta-propiolactone, formalin, ethyleneimine and binary ethyleneimine.

22. The method according to paragraph 11, 12, 13, 14, 15, 16, 17, 18, 19 or 20 wherein the culture is treated so as to recover PRRS sub-units.

23. The method according to paragraph 9, wherein the PRRS virus is propagated on the cells and one recovers an attenuated PRRS virus.

24. A PRRS virus or culture of PRRS virus obtained after propagation of PRRS virus on Cotton Rat lung cells.

25. A PRRS virus or culture of PRRS virus obtained after propagation of PRRS virus on Cotton Rat lung cell line.

26. The PRRS virus or culture of PRRS virus according to paragraph 23 or 24, wherein the cells are epithelial cells.

27. The PRRS virus or culture of PRRS virus according to paragraph 23 or 24, wherein the cells comprise epithelial cells.

28. The PRRS virus or culture of PRRS virus according to paragraph 25, wherein the cell line is the cell line deposited at the ATCC under the accession number PTA-3930 or a cotton rat lung cell line having all the identifying characteristics of the cell line deposited at the ATCC under the accession number PTA-3930.

29. The PRRS virus or culture of PRRS virus according to paragraph 25, wherein the cell line is the cell line deposited at the ATCC under the accession number PTA-3930.

30. A PRRS virus or culture of PRRS virus obtained by carrying out the method of any one of paragraphs 1 to 20 or 22.

31. The PRRS virus or culture of PRRS virus according to any one of paragraphs 23 to 28, being inactivated.

32. The PRRS virus or culture of PRRS virus according to any one of paragraphs 23 to 28, being attenuated.

33. A sub-unit PRRS virus preparation obtained by carrying out the method of paragraph 21.

34. An immunogenic composition comprising a PRRS virus or culture of PRRS virus according to any one of paragraphs 23 to 31, and a veterinary acceptable excipient, diluent or vehicle.

35. An immunogenic composition comprising a sub-unit PRRS virus preparation according to paragraph 32, and a veterinary acceptable excipient, diluent or vehicle.

36. The immunogenic composition of paragraph 33 comprising further a stabilizer.

37. The immunogenic composition of paragraph 33 or 34 or 35 comprising further an adjuvant.

38. An immunogenic composition comprising a PRRS virus culture obtained by the method according to paragraph 1.

39. An immunogenic composition comprising a PRRS virus culture obtained by the method according to paragraph 3.

40. An immunogenic composition comprising a PRRS virus culture obtained by the method according to any one of paragraphs 1 to 22.

41. A vaccine comprising a PRRS virus culture obtained by the method according to paragraph 1.

42. A vaccine comprising a PRRS virus culture obtained by the method according to paragraph 3.

43. A vaccine comprising a PRRS virus culture obtained by the method according to any one of paragraphs 1 to 22.

44. A vaccine comprising a PRRS virus or culture of PRRS virus according to any one of paragraphs 23 to 31, and a veterinary acceptable excipient, diluent or vehicle.

45. A vaccine comprising a sub-unit PRRS virus preparation according to paragraph 32, and a veterinary acceptable excipient, diluent or vehicle.

46. The vaccine of paragraph 43 comprising further a stabilizer.

47. The vaccine of paragraph 43 or 44 or 45 comprising further an adjuvant.

48. A method of immunization of a porcine comprising the administration to the porcine of an immunogenic composition according to any one paragraphs 33 to 39.

49. A method of vaccination of a porcine comprising the administration to the porcine of a vaccine according to any one paragraphs 40 to 46.

50. Cotton Rat lung cell line deposited with the ATCC under the accession number PTA-3930 or a cotton rat lung cell line having all the identifying characteristics of the cell line deposited at the ATCC under the accession number PTA-3930.

51. Cotton Rat lung cell line deposited with the ATCC under the accession number PTA-3930.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

We claim:

1. Cotton rat cell line ATCC PTA-3930 or a cell line having all the identifying characteristics thereof.

2. The cell line of claim 1 which is ATCC PTA-3930.

3. A method for producing a pathogen, organism or virus comprising propagating the pathogen, organism or virus on cells of the cell line of claim 1 or 2.

4. A method for producing a virus comprising propagating the virus on cotton rat epithelial lung cells wherein the cotton rat epithelial lung cells are isolated or cultured or from a cell line and the virus is porcine reproductive and respiratory syndrome virus (PRRSV), canine parainfluenza virus (CPI) type-2, canine adenovirus type 2, porcine bovine rotavirus (BRV) or bovine coronavirus (BCV).

5. The method of claim 4 wherein the virus is CPI type-2.

6. The method of claim 4 wherein the virus is canine adenovirus type 2.

7. The method of claim 4 wherein the virus is BRV.

8. The method of claim 4 wherein the virus is porcine BCV.

9. The method of any one of claims 4, 5-6, and 7-8 wherein the cotton rat lung cells are cotton rat cell line ATCC PTA-3930 or a cell line having all the identifying characteristics thereof.

10. The method of claim 9 wherein the cotton rat lung cells are cotton rat cell line ATCC PTA-3930.

11. A method for producing a pathogen, organism or virus comprising propagating the pathogen, organism or virus on cells of the cell line ATCC PTA-3930.

12. A method for producing a pathogen, organism or virus for an immunogenic or vaccine composition or for providing an antigen, immunogen or epitope for an immunogenic or vaccine composition, comprising propagating the pathogen, organism or virus on cotton rat lung cells from cotton rat cell line ATCC PTA-3930.

13. A method for producing a virus comprising propagating the virus on cotton rat lung cells wherein the cotton rat lung cells are isolated or cultured from a cell line and the virus is porcine reproductive and respiratory syndrome virus (PRRSV), canine parainfluenza virus (CPI) type-2, canine adenovirus type 2, bovine rotavirus (BRV), or bovine coronavirus (BCV).

14. A method for producing a virus for an immunogenic or vaccine composition or for providing an antigen, immunogen or epitope for an immunogenic or vaccine composition, comprising propagating the virus on cotton rat epithelial lung cells wherein the cotton rat epithelial lung cells are isolated or cultured or from a cell line and the virus is porcine reproductive and respiratory syndrome virus (PRRSV).

15. The method of claim 14 wherein the cotton rat lung cells are cotton rat cell line ATCC PTA-3930 or a cell line having all the identifying characteristics thereof.

16. The method of claim 15 wherein the cotton rat lung cells are cotton rat cell line ATCC PTA-3930.

17. A method for producing a virus comprising propagating the virus on cotton rat epithelial lung cells wherein the cotton rat epithelial lung cells are isolated or cultured or from a cell line and the virus is porcine reproductive and respiratory syndrome virus (PRRSV), canine parainfluenza virus (CPI) type-2, canine adenovirus type 2, porcine adenovirus type 3, bovine herpes virus type 1 (BHV-1), equine herpesvirus type 1 (EHV-1), equine herpesvirus type 4 (EHV-4), bovine parainfluenza virus type 3 (bPI-3), bovine rotavirus (BRV) or bovine coronavirus (BCV), wherein the cotton rat lung cells are cotton rat cell line ATCC PTA-3930 or a cell line having all the identifying characteristics thereof.

18. The method of claim 17 wherein the cotton rat lung cells are cotton rat cell line ATCC PTA-3930.

* * * * *